United States Patent [19]

Alexanderson

[11] 4,241,229
[45] Dec. 23, 1980

[54] RECOVERY OF NITRATED AROMATIC COMPOUNDS FROM NITRATION WASH LIQUORS

[75] Inventor: Verner Alexanderson, Sharon, Conn.

[73] Assignee: American Cyanamid Company, Stamford, Conn.

[21] Appl. No.: 64,674

[22] Filed: Aug. 8, 1979

[51] Int. Cl.³ .............................................. C07C 79/10
[52] U.S. Cl. .................................. 568/939; 568/924; 568/929; 568/940
[58] Field of Search ................ 568/924, 929, 939, 940

[56] References Cited

U.S. PATENT DOCUMENTS

| | | | |
|---|---|---|---|
| 2,256,999 | 9/1941 | Castner | 568/929 |
| 2,370,558 | 2/1945 | Mares | 568/939 |
| 3,836,601 | 9/1974 | Frey et al. | 568/930 |
| 4,091,042 | 5/1978 | Alexanderson | 568/939 |

*Primary Examiner*—Leland A. Sebastian
*Attorney, Agent, or Firm*—Frank M. Van Riet

[57] ABSTRACT

The wash liquor resulting from the nitration of aromatic compounds is contacted with a quantity of the same aromatic compound being nitrated and the resultant solution is recycled to the nitration process.

10 Claims, No Drawings

RECOVERY OF NITRATED AROMATIC COMPOUNDS FROM NITRATION WASH LIQUORS

BACKGROUND OF THE INVENTION

The nitration of aromatic compounds, especially benzene, to produce mononitrated aromatic compounds, which process is hereinafter sometimes discussed with reference to the nitration of benzene to produce mononitrobenzene, hereinafter referred to as nitrobenzene, is widely practiced commercially, particularly for the manufacture of aniline. Conventional commercial processes for nitrobenzene ordinarily utilize either a batchwise or continuous addition of a mixture of sulfuric acid and nitric acid, commonly referred to as mixed acid, to the aromatic charge material.

Representative processes for the nitration of aromatic compounds are disclosed by Castner in U.S. Pat. No. 2,256,999; and Alexanderson et al. in U.S. Pat. Nos. 4,021,498 and 4,091,042, respectively.

In these processes, and others, after the nitration reaction is completed, the spent acid, i.e., the mixed acid essentially completely depleted of nitric acid, is separated from the nitroaromatic compound layer. The crude nitroaromatic compound layer is then washed with (1) water, or (2) water containing ammonia or an alkali metal base, to remove water-soluble acidic impurities and oxidation by-products such as e.g., dinitrophenols and picric acid. The resulting wash waters, saturated with nitroaromatic compound, are normally either sewered directly, or steam stripped, or adsorbed on carbon to recover residual nitroaromatic compound before being discharged.

The direct sewering of the wash waters results in a 0.1% to 0.5% loss of yield of nitroaromatic compound and furthermore, since the effluent is not treated, it is toxic to aquatic life. The treatment of this effluent in a biological effluent treatment plant, however, is difficult because nitrated aromatic compounds are also toxic to the bacteria used therein. In view of the harmful nature of e.g., nitrobenzene, and the difficulty in treating effluents containing e.g., nitrobenzene, in modern commercial practice the nitrobenzene is usually stripped from the wash liquors with steam. This method reduces the nitrobenzene in the effluent wash water to a level acceptable for subsequent biological effluent treatment, but it is at the expense of about 40 pounds of steam per pound of nitrobenzene recovered. Thus, the stripping operation is costly in equipment and energy.

SUMMARY OF THE INVENTION

In accordance with the present invention, there is provided an improvement in a process for the mononitration of an aromatic compound with a mixed acid comprising nitric and sulfuric acid, wherein the resulting nitrated aromatic compound phase produced thereby, is recovered and washed with an aqueous solution of ammonia or an alkali to remove therefrom by-product water-soluble, ammonium or alkali metal salts, wherein the wash liquor which contains said ammonium or alkali metal salts, and a minor amount of nitrated aromatic compound, is contacted with from 0.05 to 0.5 part, by volume, of the aromatic compound being nitrated, per part by volume, of wash liquor to extract said nitroaromatic compound therefrom, and recycling the resulting solution to a aromatic compound nitration reaction.

In this manner, essentially all of the nitroaromatic compound, which is entrained in the wash liquor is recovered. Hence, the process of this invention is a practical and economic way to recover nitroaromatic compounds for recycling to an aromatic mononitration process.

DESCRIPTION OF THE INVENTION INCLUDING PREFERRED EMBODIMENTS

The improved process of the present invention is not limited to any particular nitration conditions, or any particular apparatus, or assemblage thereof, or to any particular method of operation. The process may be carried out batchwise, or continuously. For purposes of illustration, a process conducted continuously in the manner described by Alexanderson et al. U.S. Pat. No. 4,091,042 above, is used.

The process is carried out continuously using a series of four continuous-overflow, stirred-tank nitration reactors. Thus, for examle, a benzene feed stream at room temperature and a mixed acid feed steam, heated to a temperature in the range 80° C. to 120° C., are fed into the bottom of the first of the reactors to form a nitration reaction mixture which overflows and is fed into the bottom of the second reactor and so forth. The mixed acid is formed continuously in a mixing tee by blending 68.5 percent sulfuric acid and 60 percent nitric acid in amounts to provide a mixed acid containing 62.5% sulfuric acid, 5.2% nitric acid, and 32.3% water. The contents of the reactors are kept under a positive pressure sufficient to keep the benzene in the liquid state. The residence time in each reactor will depend on the volume of the reaction mixture and on the feed rate and on the reaction temperature.

The reaction mixture overflowing from the fourth nitration reactor is continuously fed to a continuous phase separator where the spent acid phase is separated from the crude nitrobenzene phase. The spent acid phase is then reconcentrated using a vacuum-flash evaporator, utilizing the heat generated in the reaction. The concentration of the spent acid using flash evaporators, or other means, is old and well-known.

The crude nitrobenzene phase is then fed continuously into a multi-stage, counter-current, washer-extractor where, in the first stage, acidic components, such as entrained sulfuric acid, dinitrophenols and picric acid, are neutralized by washing one part by volume of the crude nitrobenzene phase with about 0.4 part by volume of wash water containing about 1% by weight, of an alkalizing agent such as potassium hydroxide, sodium hydroxide, sodium carbonate, ammonium hydroxide, and the like. Sufficient alkalizing wash water is used to form the alkali or ammonium salts of any acids, or nitrophenols, present therein. The resultant first alkaline wash layer is separated from the crude nitrobenzene layer which is then washed with water in a second stage to remove any residual alkaline wash liquor. The washed nitrobenzene is recovered from the resultant second alkaline wash layer which is then combined with the first alkaline wash layer to produce a wash liquor which is transferred to a third stage where it is extracted with about 0.05 to 0.5 part, by volume, of benzene, preferably about 0.1 to 0.4 part, by volume, of benzene per part by volume of the wash liquor, to recover essentially all of the nitrobenzene therein. Alternatively, the first alkaline wash layer per se may be extracted with the benzene without first being combined with said second alkaline wash layer and vice versa. The benzene extracts essentially no nitrophenols or picric acid from the wash liquor. The benzene layer is then recovered and is preferably used by recycling it to a reaction vessel where it is reacted with mixed acid to form nitrobenzene as described above. The temperature of the benzene used in the extraction step is not critical. However, it is preferable to carry out the extraction at about 35°–45° C.

The degree of removal of the nitrobenzene from the wash liquor depends on the volume of benzene used. For example, using 0.1 part, by volume, of benzene per volume of liquor, 97.3% of the nitrobenzene is extracted. Using 0.5 part, by volume, of benzene per volume of liquor, increases the amount of nitrobenzene extracted to 99.44%.

The process described herein will function with any aromatic hydrocarbon or halogen substituted aromatic hydrocarbon which is not degraded by hot sulfuric acid and whose nitration product is also stable in the presence of hot aqueous sulfuric acid, provided that the aromatic compound may be liquified at a temperature within the range of about 40°–80° C. Thus, such aromatic compounds as benzene, toluene, dimethylbenzene, halobenzene, naphthalene, methylnaphthalene, halonaphthalene, halotoluene and halomethylnaphthalene may be used herein.

The following examples are set forth for purposes of illustration only and are not to be construed as limitations in the present invention except as set forth in the appended claims. All parts and percentages are by weight unless otherwise indicated.

EXAMPLE 1

Benzene (10% stoichiometric excess) and mixed acid containing 5.2% nitric acid, 62.5% sulfuric acid and 32.3% water, are continuously mixed and fed into the bottom of the first of four continuous overflow, stirred-tank, nitration reactors. The benzene is fed at room temperature and the mixed acid is heated to 90° C. Pressure on the reactor is 65 psig. Following a residence time of 2.8 minutes in the first reactor, the reaction temperature is 132° C. ($\Delta T = 42°$ C.) and conversion of nitric acid to nitrobenzene is 91%. The reaction mixture flows into the bottom of the second reactor and, following a residence time of 2.8 minutes, the temperature is 135° C. ($\Delta T = 45°$ C.) and conversion is 98%. The reaction is continued in this manner so that the reaction mixture, following overflow from the third and fourth reactors after 2.8 minutes residence time in each reactor, has a temperature of 135.5° C. and 136° C., respectively, and a degree of conversion of 99% and 99.5%, respectively. Total residence time is 11.2 minutes.

The flow from the fourth reactor is fed into a continuous separator, where the spent acid phase is separated from the crude nitrobenzene phase.

The spent acid phase is then reconcentrated to 68% sulfuric acid in a vacuum flash evaporator operating at 90° C. and 60 mm Hg and recycled.

The crude nitrobenzene phase is continuously fed to a multi-stage, counter-current, washer-extractor, where in the first stage, entrained sulfuric acid, dinitrophenol, and picric acid are removed by contact with a 1% solution of caustic soda.

The resultant first alkaline wash layer is then separated from the neutralized nitrobenzene which is then washed with water in a second stage. The resultant second wash layer is then separated from the neutralizer, washed nitrobenzene and combined with the first alkaline wash layer to produce a wash liquor which contains sodium salts of sulfuric acid, dinitrophenols, and picric acid, as well as residual nitrobenzene. This wash liquor is then extracted with benzene in a third stage, using 0.5 part, by volume, of benzene per part, by volume, of the wash liquor. The resultant aqueous phase is then separated and the remaining benzene phase, containing about 95%–99% of the nitrobenzene originally present in the wash liquor, is recycled to a benzene nitration reaction.

The neutralized, washed nitrobenzene is steam stripped to remove unreacted, excess benzene which is recovered and used in subsequent benzene extractions.

EXAMPLE 2

The process of Example 1 is carried out using amounts of benzene and mixed acid to produce 15,000 lbs. of crude nitrobenzene per hour, which requires 6,000 lbs. of 1% caustic soda per hour and 3,000 lbs. of water wash per hour. Analysis of the combined first and second wash layers (wash liquor) indicates that 39.75 lbs. of nitrobenzene are carried into the wash liquor per hour. Extraction of the wash liquor with 0.5 part, by volume, of benzene per hour per part, by volume, of wash liquor per hour over a period of 8 hours resulted in the recovery of 316.219 lbs. of nitrobenzene. Based on an annual operating schedule of 8,000 hours, this amounts to a recovery of 316,219 lbs. of nitrobenzene per year.

EXAMPLE 3

A synthetic wash liquor is prepared by adding sodium hydroxide (30.0 grams) and mononitrobenzene (100 mls), hereafter abbreviated MNB, to distilled water (3000 mls), heating the mixture to 45° C. and stirring for one hour, allowing the two phases to separate for 0.5 hour, and splitting off the excess MNB in a heated separatory funnel at 45° C. To the residual aqueous phase is added 2,4-dinitrophenol (25 mgs), hereafter abbreviated DNP, to provide a stock solution containing 1.606 mgs of MNB/ml and 0.0096 mg of DNP/ml.

A portion (500 mls) of the stock solution at 45° C. and benzene (50 mls) at 23° C. are charged to a round-bottom flask equipped with baffles and agitated for 0.5 hour while maintaining the temperature at 45° C. The phases are then allowed to separate and are sampled, directly following which the volume of the remaining solution is measured in a separatory funnel at 35° C. Analysis shows that the benzene phase contains no defectable DNP and 16.9 mg of MNB/ml and the aqueous phase contains 0.00924 mg of DNP/ml and 0.043 mg of MNB/ml.

Table I shows the percentages of the total DNP and MNB in each phase.

TABLE I

| | Vol. ml | DNP Weight mg/ml | DNP Weight mg | MNB mg/ml | MNB Weight mg | % of Total Each Phase DNP | % of Total Each Phase MNB |
|---|---|---|---|---|---|---|---|
| Starting Solution | 500 | 0.0096 | 4.8 | 1.606 | 803 | | |
| Aqueous Phase | 495 | 0.00924 | 4.57 | 0.043 | 21.3 | 100.0 | 2.7 |
| Benzene Phase | 45 | ND$^{(a)}$ | — | 16.9 | 760.5 | 0 | 97.3 |
| Total | | | 4.57 | | 781.8 | | |

TABLE I-continued

|  | DNP | | MNB | | % of Total | |
|---|---|---|---|---|---|---|
| Vol. | | Weight | mg/ | Weight | Each Phase | |
| ml | mg/ml | mg | ml | mg | DNP | MNB |
| Account-ability % | | 95.2 | | 97.4 | | |

$(a)$ND = not determined

EXAMPLES 4 & 5

Aliquots (500 mls) of another synthetic wash liquor are extracted with benzene (200 mls, and 250 mls, respectively) in Examples 4 and 5, respectively. The analysis of the starting solution and the results obtained with these extractions are shown in Table II.

TABLE II

|  | DNP | | MNB | | % of Total | |
|---|---|---|---|---|---|---|
| Vol. | | Weight | | Weight | Each Phase | |
| ml | mg/ml | mg | mg/ml | mg | DNP | MNB |
| Starting Solution Example 4 | 500 | 0.00993 | 4.97 | 1.308 | 654.0 | | |
| Aqueous Phase | 496 | 0.00915 | 4.54 | 0.009 | 4.6 | 100 | 0.7 |
| Benzene Phase | 197.5 | ND | — | 3.22 | 636.0 | — | 99.3 |
| | | | 4.54 | | 640.6 | | |
| Example 5 | | | | | | | |
| Aqueous Phase | 497 | 0.00912 | 4.53 | 0.0068 | 3.4 | 100 | 0.56 |
| Benzene Phase | 248 | ND | — | 2.4 | 595.2 | — | 99.44 |
| | | | 4.53 | | 598.6 | | |

These results show that essentially all of the MNB is extracted into the benzene phase with the proper benzene-to-water ratio.

EXAMPLE 6- 8

The substitution of (6) toluene, (7) dimethylbenzene and (8) naphthalene, respectively, for the benzene of Example 1 both as a charge material and an extractant, resulted in the production of the corresponding mononitro compound in yields comparative thereto.

I claim:

1. In a process for the mononitration of an aromatic hdyrocarbon with a mixed acid comprising nitric and sulfuric acid, wherein the resulting aqueous, spent-acid phase is separated from the nitroaromatic compound phase produced thereby, and wherein the nitroaromatic compound phase is washed with an aqueous solution of ammonia or an alkali to produce thereby an alkaline wash layer containing by-products as water-soluble ammonium, or alkali metal salts and nitroaromatic compound, the improvement which comprises: contacting said alkaline wash layer which contains said by-products, with from 0.05 to 0.5 part by volume of said aromatic compound being nitrated per part by volume of wash layer to extract said nitroaromatic compound therefrom, and recycling the resulting aromatic solution of nitroaromatic compound to a nitration reaction.

2. The process of claim 1 wherein the alkaline wash layer is extracted with about 0.1 to 0.4 part by volume of aromatic compound per part by volume of said layer.

3. The process according to claim 1 wherein the extraction is carried out at about 35°–45° C.

4. The process according to claim 2 wherein the extraction is carried out at about 35°–45° C.

5. The process of claim 1 wherein the aromatic compound is benzene.

6. The process of claim 1 wherein crude nitrated aromatic compound is recovered from said alkaline wash layer, the crude nitrated aromatic compound is washed with water to produce washed nitrated aromatic compound and a second alkaline wash layer, the alkaline wash layer and second alkaline wash layer are combined to form a wash liquor and the wash liquor is extracted with said aromatic compound.

7. The process of claim 6 wherein the wash liquor is extracted with about 0.1 to 0.4 part by volume of aromatic compound per part of said liquor.

8. The process of claim 6 wherein the extraction is carried out at about 35°–45° C.

9. The process of claim 7 wherein the extraction is carried out at about 35°–45° C.

10. The process of claim 6 wherein the aromatic compound is benzene.

* * * * *